US011447524B2

(12) United States Patent
Fears et al.

(10) Patent No.: US 11,447,524 B2
(45) Date of Patent: Sep. 20, 2022

(54) MULTIFUNCTION CYCLIC PEPTIDE POLYMER NANOMATERIALS

(71) Applicant: The Government of the United States of America, as represented by the Secretary of the Navy, Arlington, VA (US)

(72) Inventors: Kenan P. Fears, Alexandria, VA (US); Manoj K. Kolel-Veetil, Alexandria, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/952,876

(22) Filed: Nov. 19, 2020

(65) Prior Publication Data
US 2021/0147479 A1 May 20, 2021

Related U.S. Application Data

(60) Provisional application No. 62/937,475, filed on Nov. 19, 2019.

(51) Int. Cl.
*A61K 38/00* (2006.01)
*C07K 5/12* (2006.01)
*C07K 7/02* (2006.01)
*A01N 43/713* (2006.01)

(52) U.S. Cl.
CPC .............. *C07K 5/12* (2013.01); *A01N 43/713* (2013.01); *C07K 5/123* (2013.01); *C07K 7/02* (2013.01)

(58) Field of Classification Search
CPC ........ A01N 43/713; C07K 5/12; C07K 5/123; C07K 7/02; C07K 7/64; C07K 5/126; Y02P 20/55
See application file for complete search history.

(56) References Cited

U.S. PATENT DOCUMENTS

| | | | |
|---|---|---|---|
| 7,288,623 B2 * | 10/2007 | Ghadiri | C07K 7/64 530/317 |
| 8,975,368 B2 | 3/2015 | Kulp, III et al. | |
| 2011/0046345 A1 | 2/2011 | Kulp et al. | |

OTHER PUBLICATIONS

Fears et al., "High-performance nanomaterials formed by rigid yet extensible cyclic β-peptide polymers" Nat. Comm. 9, 4090 (Oct. 5, 2018).
Cortez-Diaz, M. D. et al., "Design, synthesis, and characterization of new cyclic D,L-α-alternate amino acid peptides by capillary electrophoresis coupled to electrospray ionization mass spectrometry", Analytical biochemistry, 2016, vol. 502, pp. 8-15.
Jagtap, P. K. A. et al., "Rational design of cyclic peptide inhibitors of U2AF homology motif (UHM) domains to modulate pre-mRNA splicing", Journal of medicinal chemistry, Oct. 18, 2016, vol. 59, No. 22, pp. 10190-10197.
Silk, M. R. et al., "Controlled construction of cyclic D/L peptide nanorods", Angewandte chemie, Jan. 8, 2019, vol. 131, No. 2, pp. 606-611.
Search Report and Written Opinion in PCT/US2020/061297 (Mar. 12, 2021).

* cited by examiner

*Primary Examiner* — Aradhana Sasan
*Assistant Examiner* — Mercy H Sabila
(74) *Attorney, Agent, or Firm* — US Naval Research Laboratory; Joseph T. Grunkemeyer

(57) ABSTRACT

Disclosed herein is a cyclic peptide polymer. $R^1$, $R^2$, and $R^3$ are organic groups. Each $R^4$ is a covalent bond, methylene, ethylene, n-propylene, or n-butylene. Each X is —NH—, —O—, or —O—CO—. The values m and n are nonnegative integers having a sum of at least 1. The value p is an integer greater than 1. The cyclic peptide polymer may be made by providing a first cyclic peptide monomer having a protecting group on the X group, covalently binding the —CO—OH group of the first cyclic peptide monomer to a solid support having a carboxylic acid-reactive group, converting the protecting group to —XH, reacting the —XH group with the —CO—OH group of an additional cyclic peptide monomer, optionally repeating the converting and reacting steps with further additional cyclic peptide monomers, and cleaving the cyclic peptide polymer from the solid support.

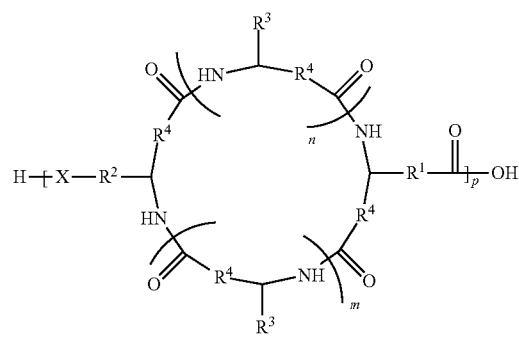

16 Claims, 13 Drawing Sheets

4

5

6

7

Minimum inhibitory concentration (µg mL$^{-1}$) against *S. aureus*

Cyclo[Lys-Ile-Phe-Glu-Trp-Lys]
(protected Lys)

Tri-cyclo[Lys-Ile-Phe-Glu-Trp-Lys]
(protected Lys)

Tri-cyclo[Lys-Ile-Phe-Glu-Trp-Lys]
(deprotected Lys)

MULTIFUNCTION CYCLIC PEPTIDE POLYMER NANOMATERIALS

This application claims the benefit of U.S. Provisional Application No. 62/937,475, filed on Nov. 19, 2019. The provisional application and all other publications and patent documents referred to throughout this nonprovisional application are incorporated herein by reference.

TECHNICAL FIELD

The present disclosure is generally related to polymers of cyclic peptides.

DESCRIPTION OF RELATED ART

Cyclic peptide rings have a stable flat, disk-like conformation with the amino acid side chains predictably displayed around the exterior or interior of the ring. These disks assemble, through hydrogen bonding, into nanoscale tubes (Ghadiri et al. *Nature*, 1993, 366, 324-327). Any disruption to the stabilizing hydrogen bonding causes disassembly of the tube structure (Rubin et al. *ACS Nano*, 2015, 9, 3360-3368). Although reassembly is possible, the sequential order of the disks is never recovered, as there are no covalent linkages between the rings to preserve such an order. A previous method disclosed the polymerization of a plurality of cyclic peptide rings containing two exteriorly displayed carboxylic acid functionalities and a plurality of peptide rings containing two exteriorly displayed amine functionalities (U.S. Pat. No. 8,975,368; Fears et al. *Nature Communications*, 2018, 9, 4090) that yielded peptide nanotube polymers containing covalent linkages.

BRIEF SUMMARY

Disclosed herein is cyclic peptide polymer having the structure I. Each $R^1$, each $R^2$, and each $R^3$ is an independently selected organic group. Each $R^4$ is independently selected from covalent bond, methylene, ethylene, n-propylene, and n-butylene. Each X is independently selected from —NH—, —O—, and —O—CO—. The values m and n are nonnegative integers having a sum of at least 1. The value p is an integer greater than 1.

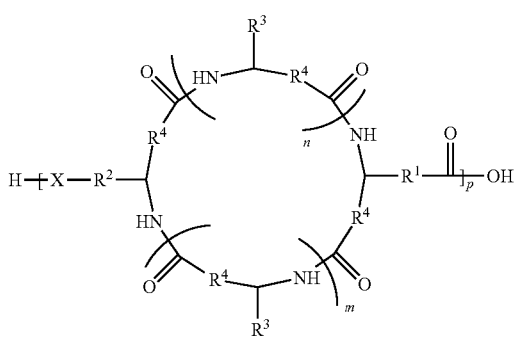

I

Also disclosed herein is method of making the cyclic peptide polymer I comprising: providing a first cyclic peptide monomer having the general structure II, covalently binding the —CO—OH group of the first cyclic peptide monomer to a solid support having a carboxylic acid-reactive group, converting the —X—Y group to —XH, reacting the —XH group with the —CO—OH group of an additional cyclic peptide monomer having the same general structure as the first cyclic peptide monomer, optionally repeating the converting and reacting steps with further additional cyclic peptide monomers, and cleaving the cyclic peptide polymer from the solid support. Y is a protecting group. $R^1$, $R^2$, $R^3$, $R^4$, X, Z, m, and n are as defined above, those of the additional cyclic peptide monomer may be the same or different from those of the first cyclic peptide monomer.

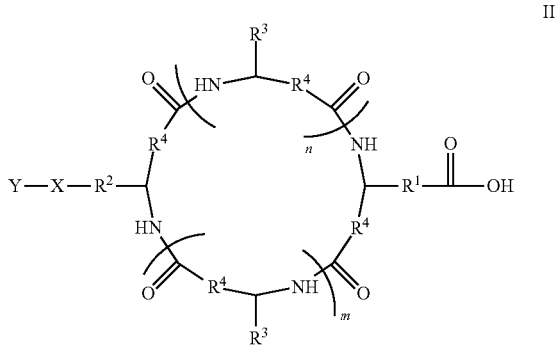

II

Also disclosed herein is a cyclic peptide having the structure III. $R^1$, $R^2$, $R^3$, $R^4$, X, m, and n are as defined above. Each Y is independently selected from H and a protecting group.

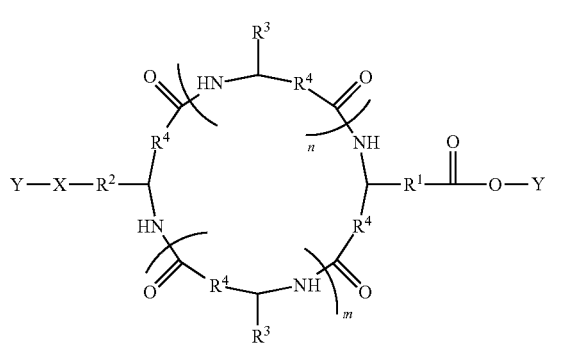

III

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

Figure 1:
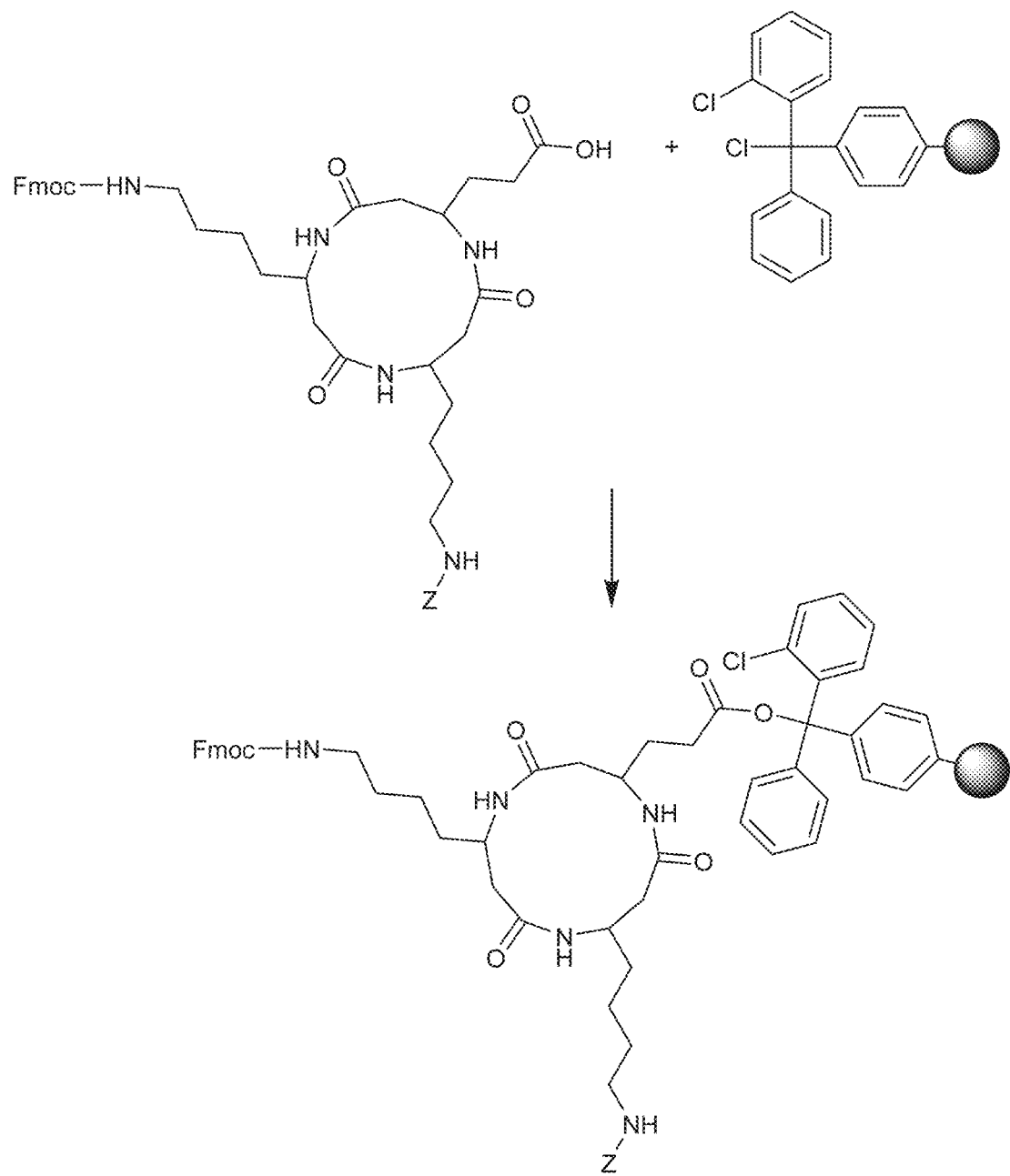
FIG. 1 shows bonding of an example cyclic peptide to a support.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Described herein are methods of linking cyclic peptide monomers into peptide nanotube polymers containing covalently bonded cyclic peptide units/rings. The chemical, physical, and functional properties of the resulting polymers can be tailored by varying design parameters (i.e., cyclic peptide size, linkage length) and displayed side chain chemistries, or through the conjugation or coordination of other peptides, polymers, atoms, atom complexes, nanoparticles, and/or inorganic compounds. The methods involve the polymerization of a plurality of peptide rings that exteriorly display both a single carboxylic acid functionality and a single amine functionality on the same ring.

The polymerization of cyclic peptide rings can either be undertaken in bulk, as previously described (U.S. Pat. No. 8,975,368; Fears et al. *Nature Communications*, 2018, 9, 4090), or by ring-by-ring addition by adding a protection group to an amine or carboxylic acid functionality and then sequentially adding rings in a manner analogous to the solid phase peptide synthesis of linear peptides. While the polymerization in bulk yields peptide nanotubes with lengths that are statistically distributed, the ring-by-ring addition method provides a means to control the length of the peptide nanotubes to desired values, which is especially important while synthesizing peptide nanotube polymers that can precisely insert into biological membranes such as lipid bilayers. This method also affords control over the sequential addition of rings displaying different chemistries, allowing for the predictable lateral and axial display of chemistries from nanotubes. In addition to utilizing the reaction between amine and carboxylic acid groups to form covalent links between cyclic peptide rings, the method also provides routes to produce linkages such as ester, anhydride, dithiol, etc. via the reactions of appropriate functional groups contained in the reacting cyclic peptide ring units. This method allows for the combination of robust linkages, and linkages that can be readily cleaved through hydrolysis, reduction, photoexcitation, enzymatic degradation, or changes in environmental conditions such as pH, temperature, or solvent composition.

The physical and chemical properties of the exterior and interior of cyclic peptide polymer nanotubes can be altered through the selection of displayed chemistries. Rings can consist of natural or unnatural α-, β-, γ-, δ-, or ε-amino acids, or a combination thereof. The self-assembly of cyclic peptide polymers into rigid nanomaterials can be modulated by controlling the electrostatic characteristics of neighboring subunits. Due to their strong dipole moment when assembled into rigid nanomaterials, external electromagnetic stimulation can also influence the conformation and nanodimensionality of cyclic peptide polymers.

The reactive termini displayed on cyclic peptide rings may be functionalized by polymeric and/or peptide chains through common addition and condensation polymerization methods such as free radical, cationic, anionic, chain initiation, chain propagation, chain termination, coordination, ring opening, chain transfer, metathesis, ADMET, etc. to provide novel peptide-polymer or peptide-peptide conjugates. Furthermore, organic-inorganic conjugates can be formed through the chemical ligation or coordination of single atoms, atom complexes, nanoparticles, and/or inorganic compounds to functional groups displayed by either the cyclic peptide rings or polymeric/peptide chains attached to cyclic peptide rings. Composite materials consisting of cyclic peptide polymers and other organic and/or inorganics compounds may also be made.

The synthesis method uses a cyclic peptide with the general structure III. Methods for making cyclic peptides are known in the art and some methods are disclosed in U.S. Pat. No. 8,975,368 and Fears et al. *Nature Communications*, 2018, 9, 4090. It is expected that such procedures will produce the desired cyclic peptide regardless of the amino acid sequence. The cyclic peptide is made from a corresponding linear polymer. In one method, the COOH group of the first amino acid in the sequence is bound to a solid support, such as 2-chlorotrityl chloride resin (Lapatsanis et al., "Synthesis of n-2,2,2-(trichloroethoxycarbonyl)-1-amino acids and n-(9-fluorenylmethoxycarbonyl)-1-amino acids involving succinimidoxy anion as a leaving group in amino-acid protection" *Synthesis*, 671-673, (1983)). The amino group of the amino acid as well as any reactive side groups may be bound to protecting groups to ensure that only the acid group reacts with the resin. Then the amino-protecting group is removed. One by one, the amino-protected amino acids are added to the growing peptide and their amino-protecting groups removed. When the full linear peptide has been formed, it is cleaved from the resin and allowed to cyclize. Performing the cyclization at low concentrations can promote cyclization of the individual short peptides as opposed to formation of linear polymers or cyclic polymers from more than one of the short peptides.

In structure III, the sum of m and n is at least 1, so that the cyclic peptide is made from at least 3 amino acids. The values m and n may be equal or nearly equal so that the amino acids that bind to the next cyclic peptide are on or near opposite sides of the cyclic peptide. Suitable values for m and n include, but are not limited to, 0, 1, and 2. Any natural or synthetic amino acids may be used. Any combination of α-, β-, γ-, δ-, ε-amino acids (corresponding to the $R^4$ groups being covalent bond, methylene, ethylene, n-propylene, n-butylene respectively) may be used. The use of β-amino acids may promote cyclization, as the peptide will naturally have a curved shape. The amino acids may be D- or L-amino acids in any combination. The use of alternating D- and L-amino acids may promote cyclization, as this peptide will also naturally have a curved shape.

The $R^1$, $R^2$, and $R^3$ groups are the side chains of the amino acids and may be any organic groups, including those found in naturally occurring amino acids and typical synthetic amino acids. $R^1$ is bound to a terminal carboxylic acid group, as is found in glutamic acid. $R^2$ is bound to an acid-reactive group, such as the amino group in lysine. $R^2$ may also terminate in a hydroxyl group or a carboxylic acid group. Any $R^3$ groups that are reactive with the resin or other amino acids may include protecting groups. An example amino-protecting group is carboxybenzyl (Z, Cbz), formed by reacting the amino group with benzyl chloroformate and removed by hydrogenation in methanol using palladium on activated charcoal as a catalyst. Another amino-protecting group is fluorenylmethyloxycarbonyl (Fmoc), formed by reacting the amino group with 9-fluorenylmethylsuccinimidyl carbonate (Fmoc-OSu) and removed with a base such as piperidine. An example acid-protecting group is tert-butyloxycarbonyl (Boc), formed by reacting the acid group with di-tent-butyl dicarbonate and removed with trifluoroacetic acid (TFA). Other protecting groups and their methods of addition and removal are known in the art and may be used.

Figure 2:
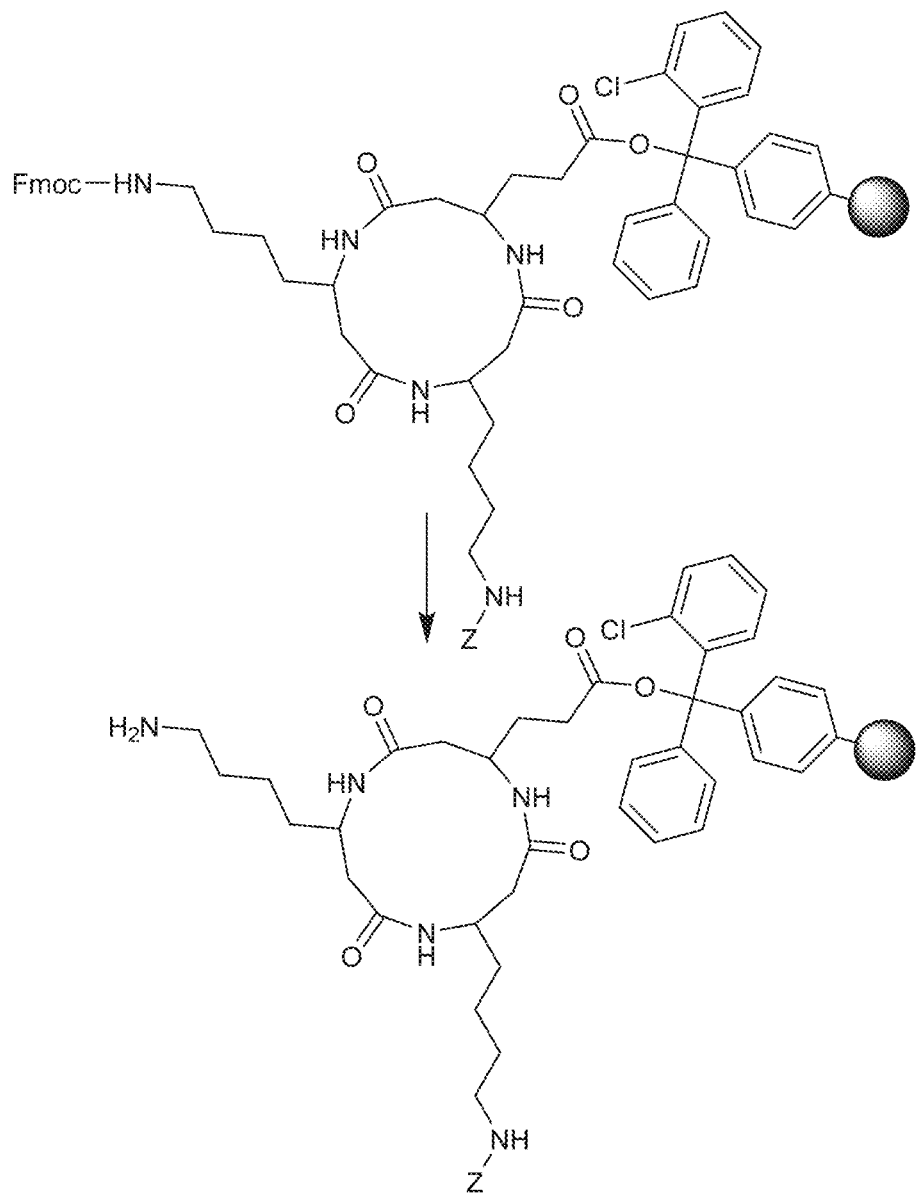
FIG. 2 shows deprotection of an amino group on the cyclic peptide.
Figure 3:
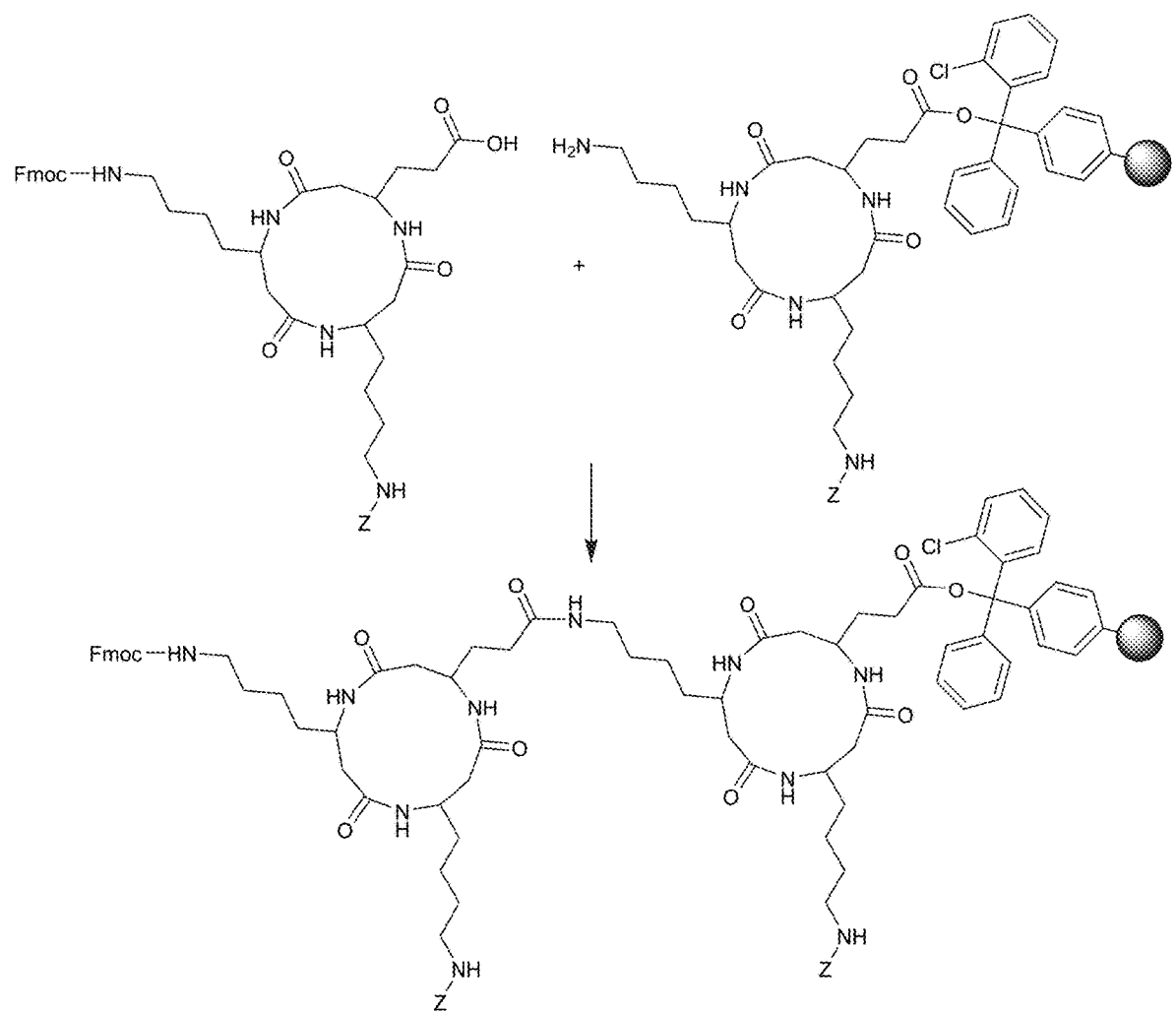
FIG. 3 shows extension of the cyclic peptide polymer.
Figure 4:
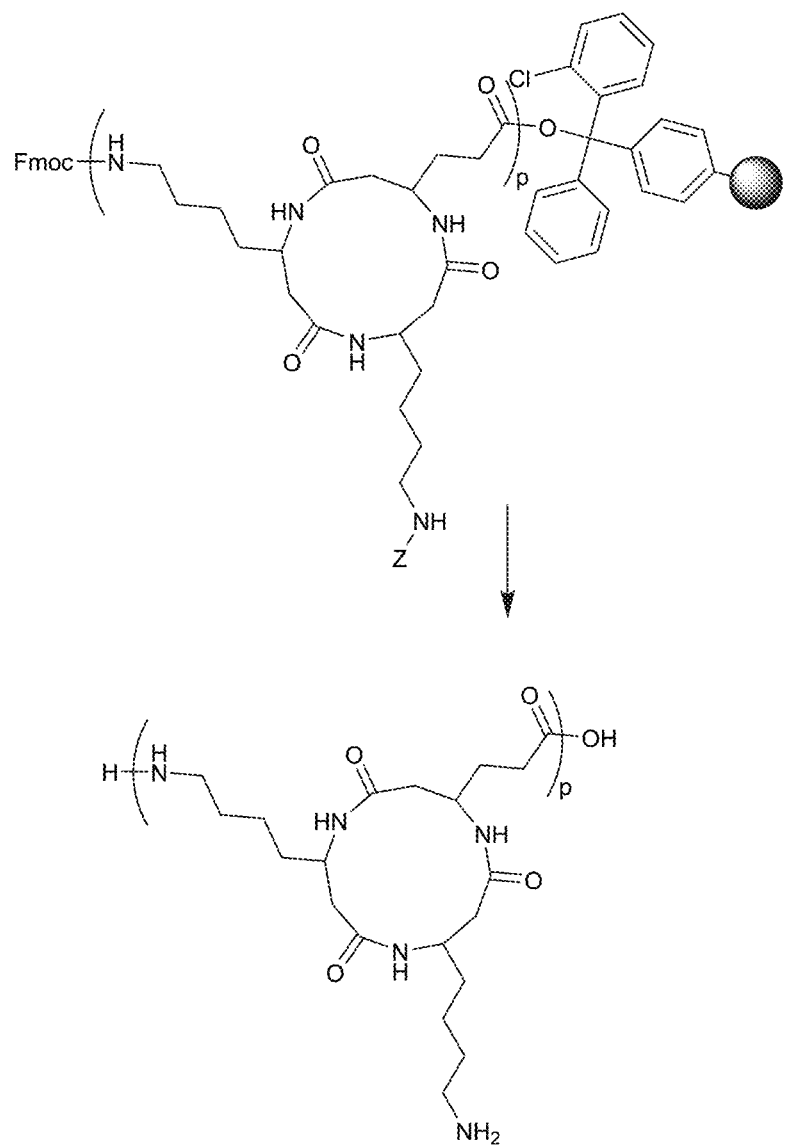
FIG. 4 shows cleavage of the cyclic peptide polymer from the support.
Figure 5:
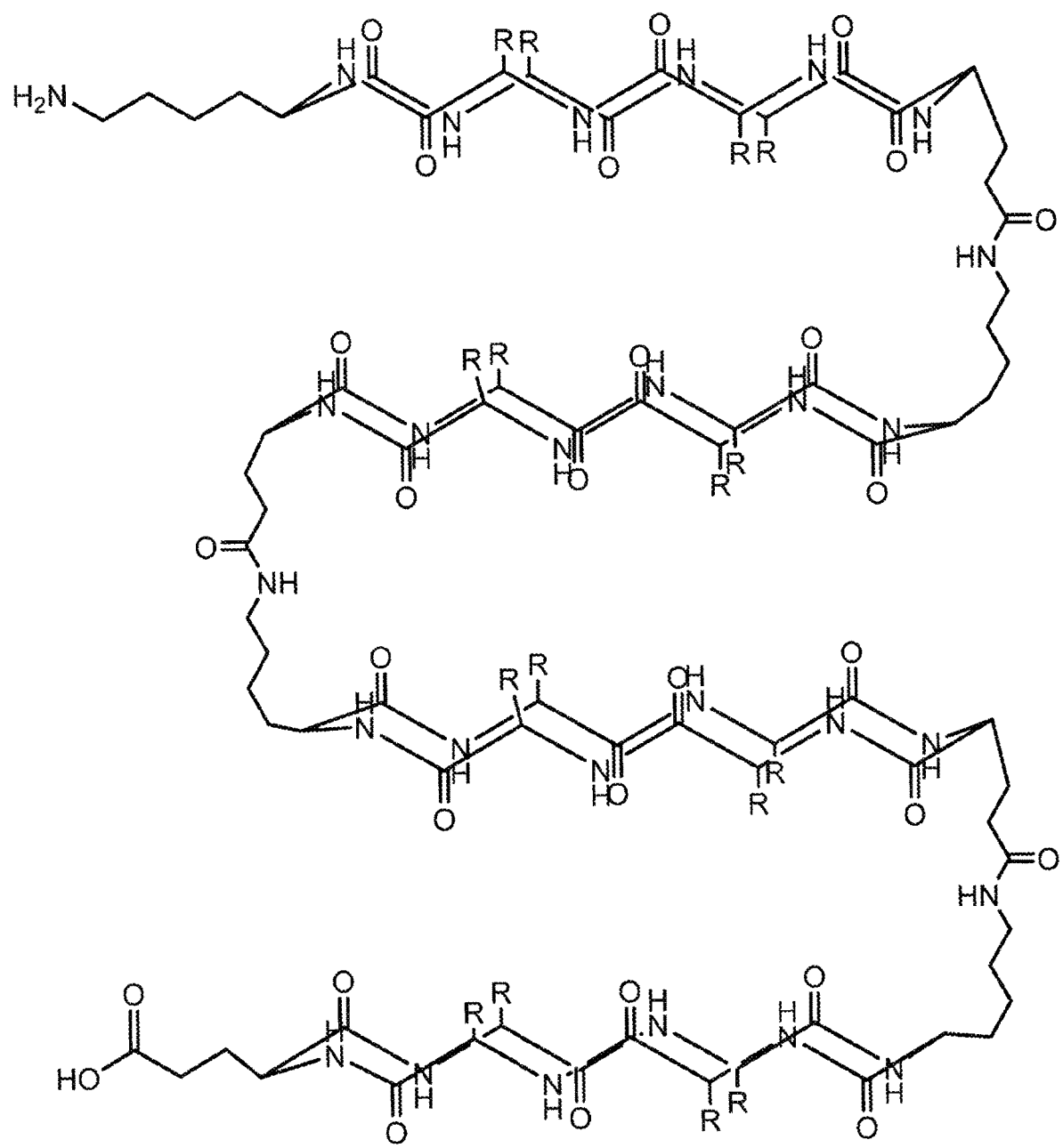
FIG. 5 shows an example of a nanopore.

The —CO—OH group of the first cyclic peptide monomer is covalently bound to a solid support having a carboxylic acid-reactive group. One suitable support is 2-chlorotrityl chloride resin. An example reaction is shown in FIG. 1. Next, the amino group is deprotected as shown in FIG. 2. Another cyclic peptide is bound to the amino group as shown in FIG. 3. The steps in FIGS. 2 and 3 may be repeated to produce a desired number of rings in the polymer. Finally, the polymer is cleaved from the support and all protecting groups are removed as shown in FIG. 4. The cleaved polymer may spontaneously fold itself into a nanopore configuration as shown in FIG. 5 (All side groups shown as R).

The method described herein provides a procedure for preparing cyclic peptide nanotube polymers (PNPs) wherein each cyclic peptide ring is covalently linked individually to both of its neighboring cyclic peptide rings. Furthermore, the method also provides a way to control the length of the produced PNP. This method provides many potential advantages.

The PNPs can be produced by polymerizing a plurality of cyclic peptide rings derived from α-, β- γ-, δ-, and/or ε-amino acids. Such versatility in the nature of cyclic peptide rings can yield PNPs that have enhanced tunability in pore sizes, dipole moment, and surface and morphological characteristics. For example, within the cyclic peptide ring the α-, β- γ-, δ-, and/or ε-amino acid can be situated in a block or random fashion.

PNPs can be made from cyclic peptide rings that contain both an amino group and a carboxylic group on the same ring that react with similar corresponding reactive groups in other cyclic peptide rings to form covalent linkages. Additionally, the cyclic peptide rings can also contain carboxylic groups and hydroxyl groups, which produce ester and anhydride covalent linkages between cyclic peptide rings upon reaction. Also, thiol groups on the cyclic peptide rings can react to form disulfide covalent linkages. In essence, any two mutually reactive functional groups on neighboring cyclic peptide rings can react to form covalent linkages between the rings.

Two routes for forming PNPs are disclosed wherein in the first route there is no control over the length of the polymer formed while in the second route the length of the cyclic peptide nanotube polymers can be precisely controlled. In the first case, the polymerization is carried out in bulk whereas in the second case the polymers are formed using a solid phase synthesis procedure such as used in synthesis of linear peptides. In the solid phase synthesis, either the amine or the carboxylic group of an incoming reactive cyclic peptide ring can be protected to leave the unprotected group to react and extend the chain length. This way, there is absolute control over the length of the produced PNP which is very advantageous for biomedical and nanotechnological applications.

The method provides for the functionalization of displayed reactive termini with a variety of polymer or peptide entities by conventional addition and condensation polymerization techniques. This lends the ability to produce new conjugates with many possible biomedical applications such as tissue engineering.

The method provides for the conjugation or coordination of atoms, nanoparticles, complexes, compounds, or minerals with PNPs to functionalize PNPs and/or form composite materials.

The following examples are given to illustrate specific applications. These specific examples are not intended to limit the scope of the disclosure in this application.

EXAMPLE 1

Figure 6:
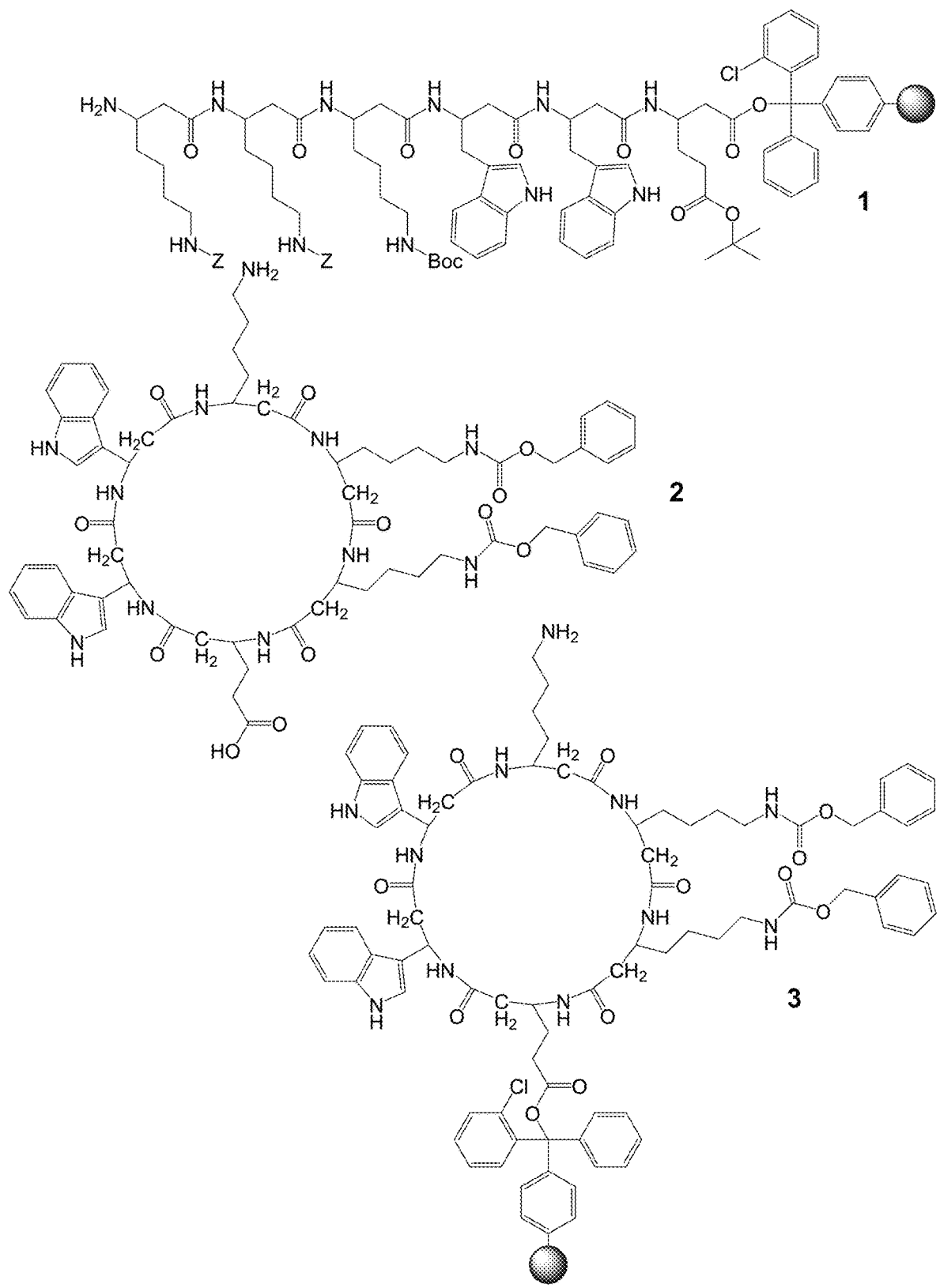
FIG. 6 shows chemical structures of a linear precursor (1), a Z-protected cyclic peptide (2), and a resin-mounted protected cyclic peptide (3).

The peptide nanopores can exhibit antimicrobial activities based on their nanodimensionality, including pore size and length and other surface characteristics. First, the linear β-peptide precursor, $NH_2$-HLys(Z)-HLys(Z)-HLys(Boc)-HTrp-HTrp-HGlu(Boc)-OH (1) was synthesized via standard solid phase peptide synthesis and cleaved from the acid-labile 2-chlorotrityl resin using 1% trifluoroacetic acid (TFA) in $CH_2Cl_2$ (FIG. 6). The precursor was then cyclized in dimethylformamide (DMF) with HATU, the Boc protecting groups were removed with TFA/water/triisopropylsilane to furnish 2. An Fmoc protecting group was added to the de-protected Lys in 2 using Fmoc-OSu. Polymers consisting of eight cyclic peptides of were formed by first attaching Fmoc-protected 2 to 2-chlorotrityl resin to furnish 3, then sequentially de-protecting the resin-bound product and coupling addition units of Fmoc-protected 2 in a manner analogous to standard solid phase peptide synthesis. The final product was produced by cleaving polymers from the resin using 1% TFA in $CH_2Cl_2$, removing the Z protecting groups by hydrogenation in methanol using palladium on activated charcoal as a catalyst, and purifying the polymer via reverse phase high performance liquid chromatography.

Figure 7:
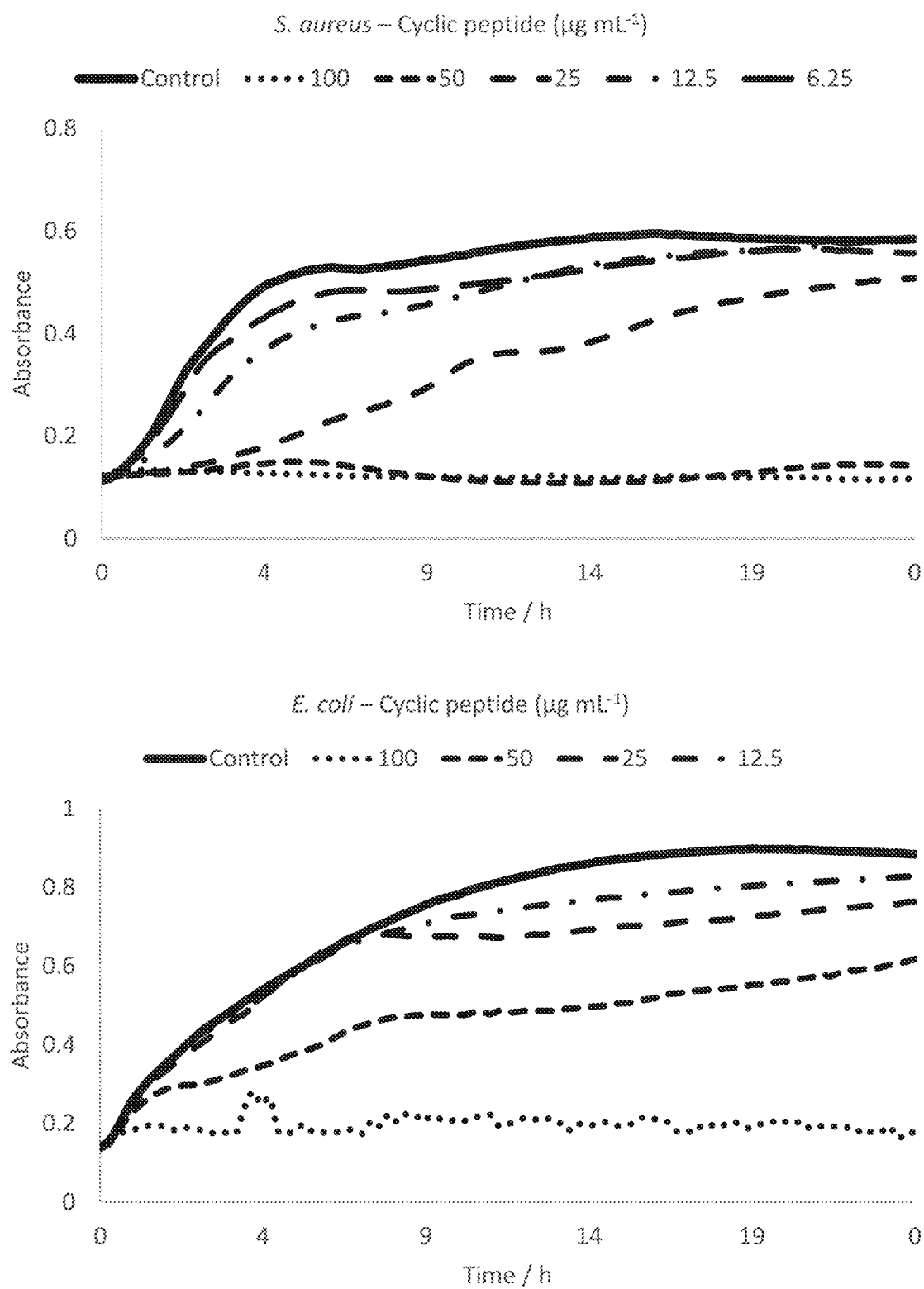
FIG. 7 shows minimum inhibitory concentration assays of cyclo[HLys-HLys-HLys-HTrp-HTrp-HGlu] against *S. aureus* and *E. coli*.

To assess antimicrobial activity, the minimum inhibitory concentrations (MICs) of the cyclic β-peptide cyclo[HLys-HLys-HLys-HTrp-HTrp-HGlu] against gram positive (Staphylococcus aureus) and gram-negative (Escherichia coli) bacteria were determined. FIG. 7 shows that the cyclic peptide is effective against both bacteria tested (S. aureus>E. coli).

Additionally, peptide nanopores can be functionalized with peptide sequences, or other antimicrobial agents, that promote recognition for bacterial cells and/or insertion into bacterial membranes to enhance the efficacy of the nanopores, or other therapeutic effects. The functionalization can occur via bonds that are robust (e.g., amide), susceptible to biodegradation (e.g., ester) for controlled-release, susceptible to degradation by external stimuli (e.g., photo-cleavable) for triggered-release, or a combination thereof.

EXAMPLE 2

Figure 8:
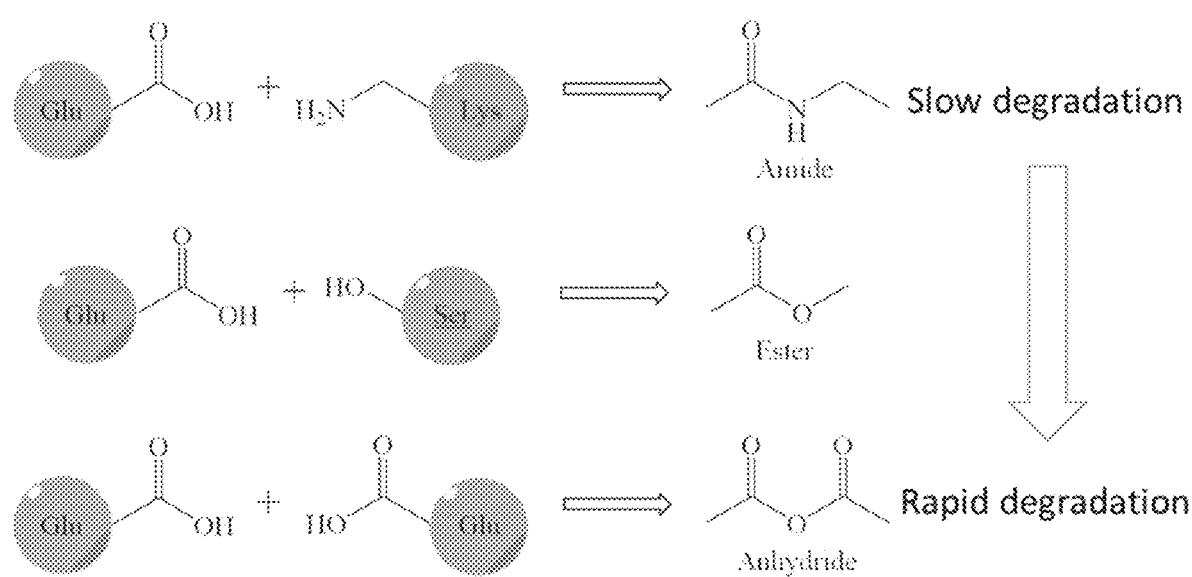
FIG. 8 shows hydrolysis susceptibility of potential linkages between cyclic peptide subunits formed via reactions between amino acid side chains.

Controlled-release antimicrobial agents can be formed by polymerizing antimicrobial nanopores, such as those described in Example 1, via degradable linkages. FIG. 8 shows amino acid side chains that can be reacted to form linkages with tunable hydrolytic susceptibility. For example, a plurality nanopores consisting of eight amide-linked cyclic peptide subunits—the first seven cyclo[HLys-HLys-HLys-HTrp-HTrp-HGlu] and the eighth cyclo[HLys-HLys-HGlu-HTrp-HTrp-HGlu] can be polymerized via the free carboxylic acid groups on the first and last subunit to form anhydride linkages between each nanopore. Also, a combination of antimicrobial nanopores bearing different side chain chemistries or functionalizations can be polymerized to form multifunctional agents that target different bacteria or have other therapeutic effects. In addition to hydrolytically degradable bonds, linkages can be formed between nanopores that are triggered by a change in environmental conditions, external stimuli, susceptible to enzymatic attack, or a combination thereof.

EXAMPLE 3

Figure 9:
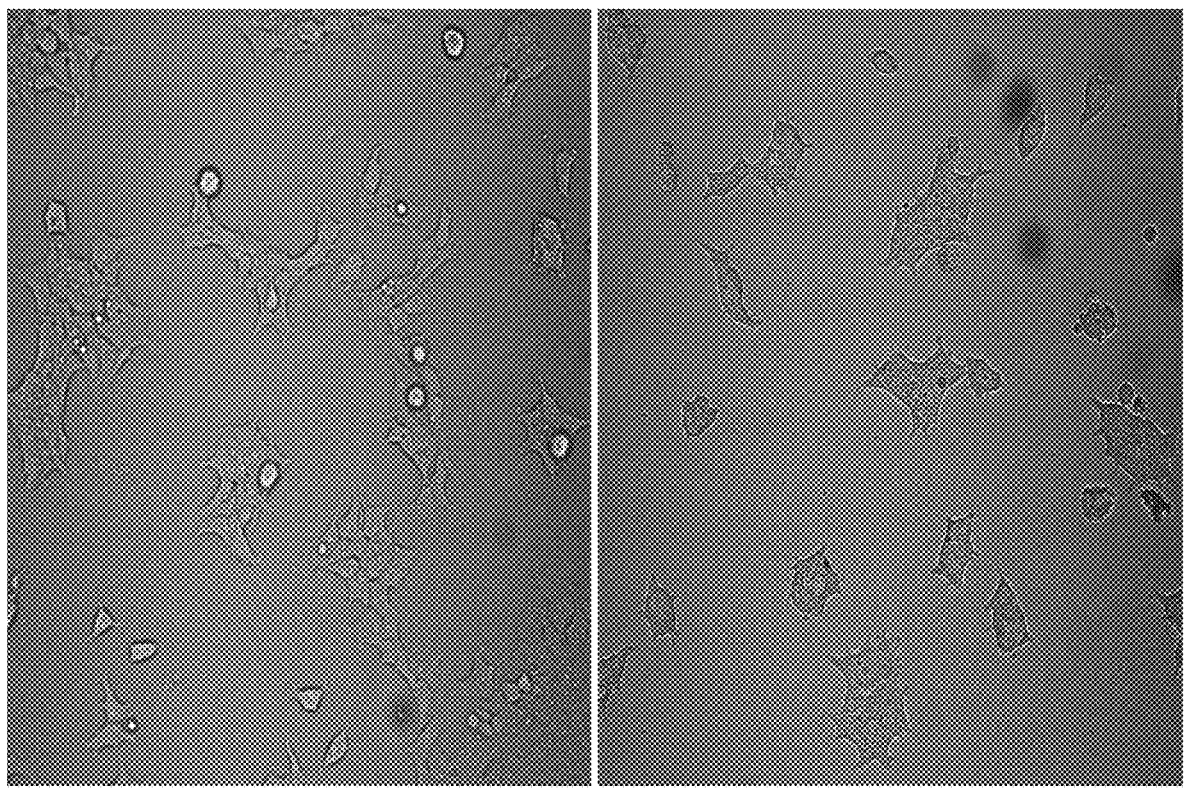
FIG. 9 shows kidney cells cultured for 24 hours on tissue culture polystyrene dishes pre-coated with a 30 μg mL$^{-1}$ fibrinogen solution (left) and a 200 μg mL$^{-1}$ cyclic β-tripeptide polymer solution (right).
Figure 10:
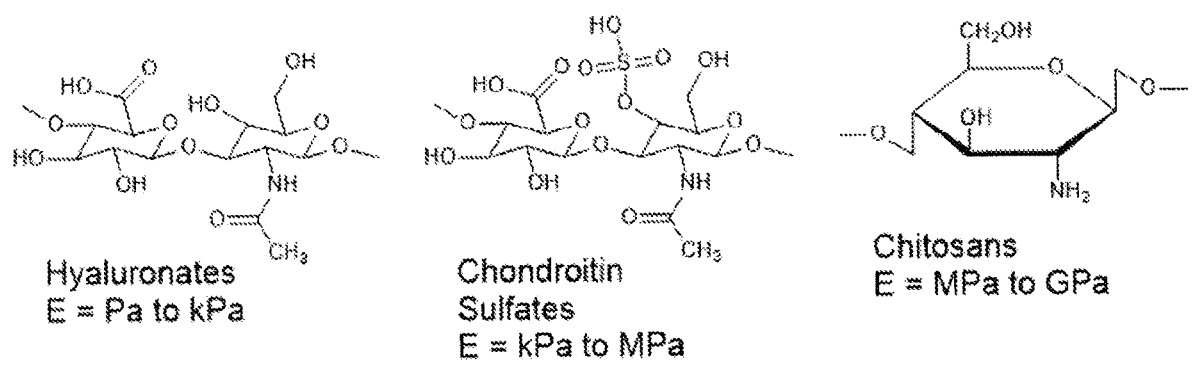
FIG. 10 shows elastic moduli range of various biogenic polysaccharides.

FIG. 9 shows kidney cells cultured for 24 hours on tissue culture polystyrene dishes pre-coated with a 30 µg mL$^{-1}$ fibrinogen solution (left) and a 200 µg mL$^{-1}$ cyclic β-tripeptide polymer solution (right). Due to the inherent biocompatibility of cyclic peptide polymers, hydrogels can be formed using these materials that mimic extracellular matrices (ECMs). The mechanical properties of artificial ECMs can be tailored by varying the subunit size (Table 1) or the linkage length between subunits (Table 2), as well as by functionalizing cyclic peptide polymers with other polymer chains or nanoparticles bearing different mechanical properties (FIG. 10). Likewise, the chemical properties of the artificial ECMs can be tailored by functionalizing the cyclic peptide polymer with other polymer chains or nanoparticles, and through the selection of amino acid chemistries displayed by cyclic peptide polymers. Cyclic peptide polymers, as well as any attached polymer chains or nanoparticles, can be functionalized with biomolecules to elicit desired responses from their intended environment. These biomolecules can include integrin binding motifs, growth factors, hormones, enzymes, and therapeutic agents that can be covalently tethered or physically entrapped within artificial ECMs. Additionally, antimicrobial agents described in Example 1 and Example 2 can be incorporated into artificial ECMs, through covalent cross-linking or physically mixing, to afford microbial resistance. Covalent linkages that are subject to hydrolytic degradation can be incorporated for the controlled-release of biomolecules and/or nanopores over time. Likewise, linkages that can be cleaved upon changes to environmental conditions, external stimuli, or enzymatic attack can be used for the triggered-release of biomolecules and/or nanopores.

TABLE 1

Comparison of the mechanical properties of cyclic β-peptide polymers, with 8 atom linkages between rings, as a function of subunit size (# of amino acids). Properties were determined by molecular dynamic simulations of 8 subunit assembles under tension.

| Size (AAs) | Modulus (GPa) | 95% C.I. | Tensile (GPa) | 95% C.I. |
|---|---|---|---|---|
| 3 | 64 | 5 | 3.4 | 0.1 |
| 4 | 52 | 2 | 2.2 | 0.4 |
| 6 | 14 | 8 | 1.1 | 0.2 |
| 8 | 14 | 1 | 1.0 | 0.3 |

| Size (AAs) | Strain (−) | 95% C.I. | Toughness (GJ m$^{-3}$) | 95% C.I. |
|---|---|---|---|---|
| 3 | 2.3 | 0.1 | 2.8 | 0.1 |
| 4 | 2.7 | 0.1 | 2.0 | 0.6 |
| 6 | 3.1 | 0.2 | 1.6 | 0.2 |
| 8 | 4.6 | 0.2 | 1.8 | 0.1 |

TABLE 2

Comparison of the mechanical properties of cyclic β-tripeptide polymers as a function of the length (# of atoms) of the linkage between rings. Properties were determined by molecular dynamic simulations of 8 subunit assembles under tension.

| Length (atoms) | Modulus (GPa) | 95% C.I. | Tensile (GPa) | 95% C.I. |
|---|---|---|---|---|
| 6 | 60 | 9 | 2.4 | 0.1 |
| 8 | 64 | 5 | 3.4 | 0.1 |
| 10 | 41 | 4 | 2.2 | 0.2 |
| 12 | 28 | 2 | 2.5 | 0.1 |

| Length (atoms) | Strain (−) | 95% C.I. | Toughness (GJ m−3) | 95% C.I. |
|---|---|---|---|---|
| 6 | 1.6 | 0.02 | 1.9 | 0.1 |
| 8 | 2.3 | 0.1 | 2.8 | 0.1 |
| 10 | 2.9 | 0.3 | 2.8 | 0.4 |
| 12 | 3.6 | 0.2 | 3.1 | 0.2 |

EXAMPLE 4

Composite materials can be formed by mixing cyclic peptide polymers with other organic and/or inorganic phases. Organic phases, such as polymer chains, can be covalently linked or physically mixed with cyclic peptide polymers. Inorganic phases, such as minerals, can be physically mixed starting from pre-formed particles or formed in the organic phases via nucleation and growth methods. Final composite materials can be produced using standard fabrication techniques, such as pressing and extrusion.

EXAMPLE 5

Through the incorporation of reactive components, such as metal atoms, complexes, and nanoparticles, the disclosed polymers can function as catalytic materials. Reactive chemistries can be covalently or non-covalently bonded to side chemistries displayed along the exterior of cyclic peptide polymer or confined within the interior. Singularly, the disclosed polymers can act as responsive, single atom catalysis platforms with nano-sized reaction spaces imparting nanoconfinement effects during catalysis. Catalytic nanopores can be formed through ring-by-ring addition, and higher molecular weight nanopolymers can be formed through batch polymerization. Furthermore, cyclic peptide polymers can function as responsive catalytic supports that modulate activity since the conformation of cyclic peptide polymers—thereby, the position of the display chemistries—can be influenced by electrostatics and electromagnetic stimuli. The disclosed cyclic peptide polymers can also be used in piezoelectric (converting mechanical to electrical) applications.

EXAMPLE 6

Figure 11:
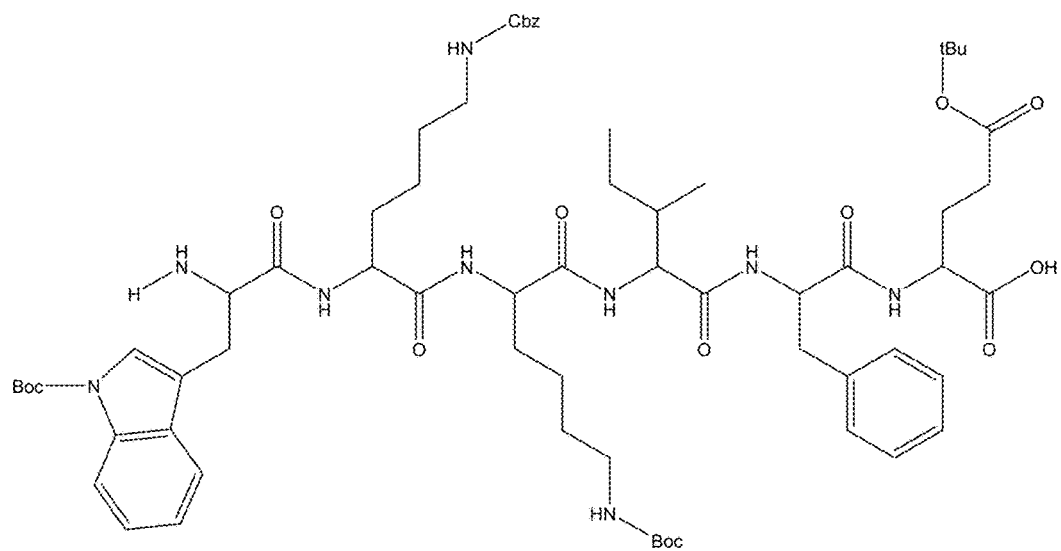
FIG. 11 shows formation of a cyclic peptide.
Figure 11:
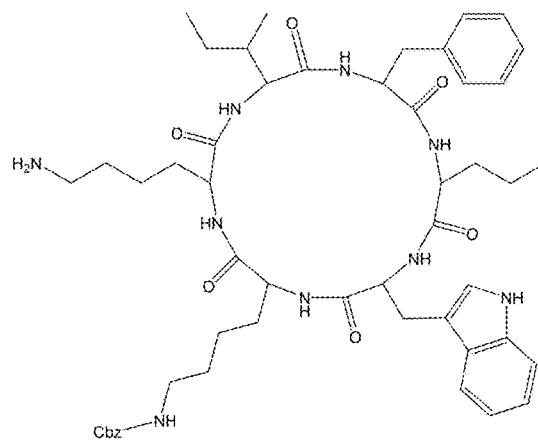
Figure 11:
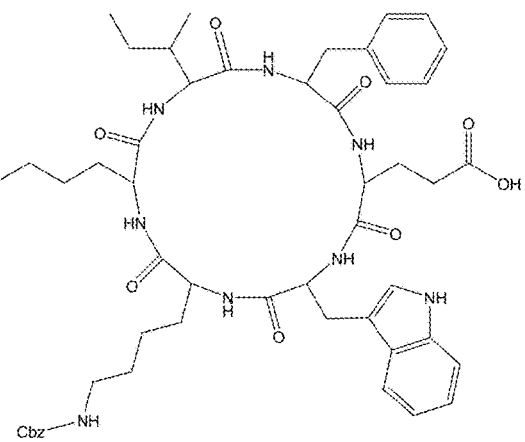
Figure 11:
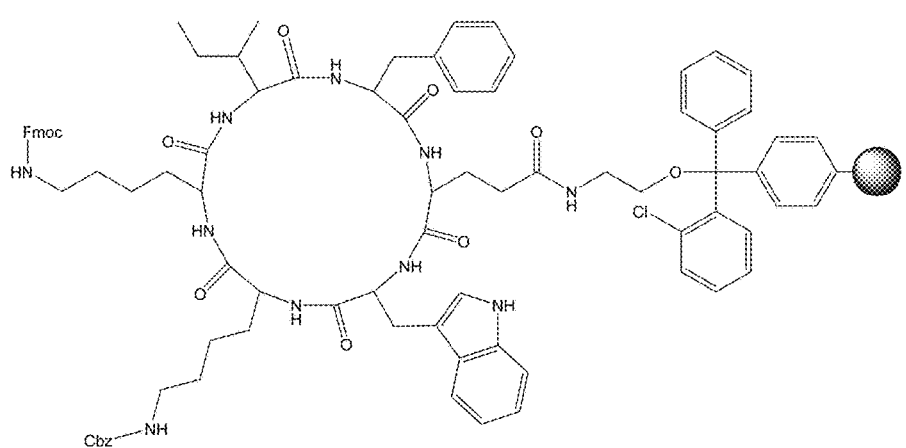
Figure 12:
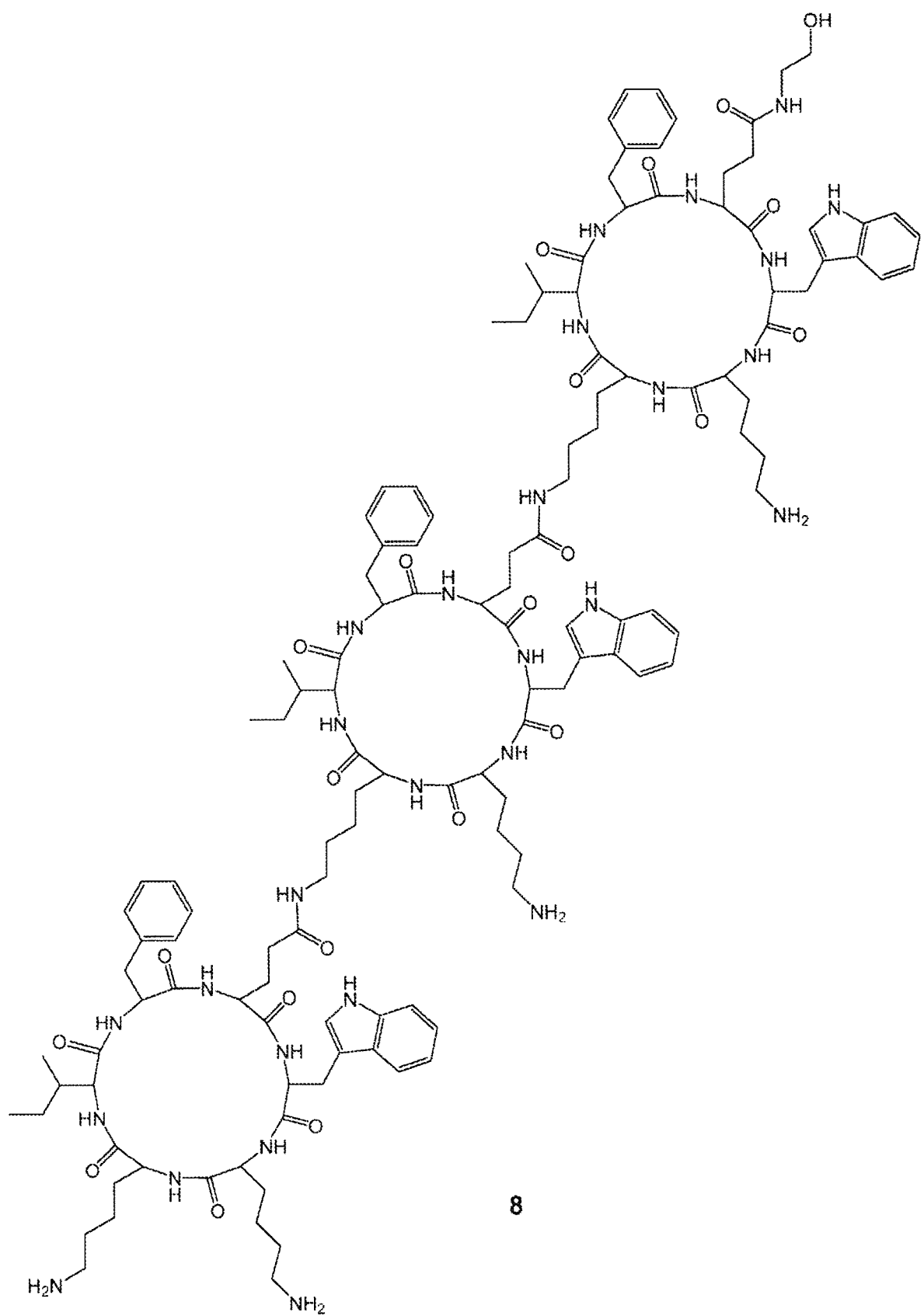
FIG. 12 shows formation of a polycyclic peptide.

The linear α-peptide, NH$_2$-L-Trp-D-Lys(Z)-L-Lys(Boc)-D-Ile-L-Phe-D-Glu(tBu)-OH was synthesized via standard solid phase peptide synthesis (SPPS). The first amino acid, Fmoc-D-Glu(tBu)-OH, was dissolved in dichloromethane (DCM) with 2,4,6-collidine. Subsequent amino acids were systematically added by de-protecting the N-terminal Fmoc groups with 20% piperidine in dimethylformamide (DMF) and coupling amino acids (3 eq.) dissolved in 20% N-methylmorpholine (NMM) in DMF using HATU (3 eq.) as the coupling agent. After coupling the last amino acid, the N-terminal Fmoc groups were de-protected and linear peptide was cleaved with 30% hexafluoroisopropanol (HFIP) in DCM to yield 4 (FIG. 11). This cleavage solution was used to preserve all side-chain protecting groups. The cleavage solution was rotovaped to remove the solvent. The crude peptide was dissolved in 20% NMM in DMF and cyclized using HATU (3 eq.) as the coupling agent. The cyclization solution was rotovaped to remove the solvent. The Boc/tBu protecting groups were removed with trifluoroacetic acid (TFA)/water/triisopropylsilane to yield 5 (FIG. 11), and the cyclic peptide was precipitated in cold diethyl. The precipitate was dissolved in acetone and an Fmoc protecting group was added to de-protected Lys by adding Fmoc-succinimide (1.2 eq.) to yield 6 (FIG. 11). The Fmoc-protected cyclic peptide was purified via reverse-phase high performance liquid chromatography (RP-HPLC). The cyclic peptides were polymerized by first coupling the cyclic peptide to glycinol 2-chlorotrityl resin with diisopropylethylamine (3 eq.) in DCM to yield 7 (FIG. 11). The Fmoc protecting group on the resin bound cyclic peptide was removed with 20% piperidine in DMF, and then another cyclic peptide was coupled using 20% NMM in DMF with HATU (3 eq.) as the coupling agent, in a manner analogous to SPPS. This process was repeated once more to obtain tri-cyclic peptide polymers, which were cleaved from the resin with 30% HFIP in DCM. The Z protecting groups were removed with 10% HBr in acetic acid to yield the final product, 8 (FIG. 12).

Figure 13:
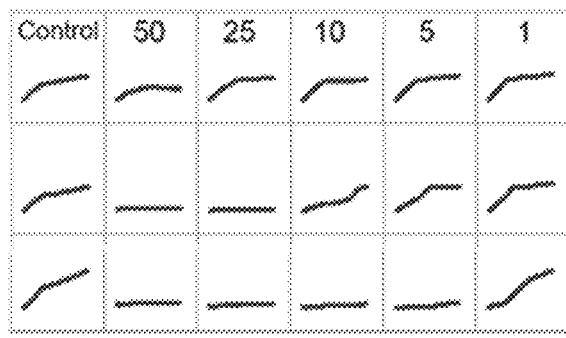
FIG. 13 shows *S. aureus* growth curves (24 hrs) in response to cyclic peptides.

To assess antimicrobial activity, the minimum inhibitory concentrations (MICs) of the monomeric de-protected cyclic peptide, Z-protected tri-cyclic peptide polymer, and de-protected cyclic peptide polymer against the gram-positive bacterium, Staphylococcus aureus (ATCC 12600), were obtained. For antimicrobial assays, S. aureus was streaked on Luria-Bertani (LB) agar plates and cultured for 24 hours at 37° C. A single colony was inoculated in a culture tube with LB broth and allowed to culture for 24 hours 37° C. on a shaker plate. After 24 hours the culture was diluted to an absorbance of ca. 0.025 O.D. at 600 nm, an approximate concentration of 5×106 cells per mL. Aliquots of the inoculum were added to wells on a 96-well plate, along with serial dilutions of the cyclic peptides being assays to determine their MICs. As shown by FIG. 13, the monomeric de-protected cyclic peptide does not completely inhibit the growth of S. aureus at 50 μg mL$^{-1}$, whereas the Z-protected tri-cyclic peptide polymer inhibits growth at 25 μg mL$^{-1}$, as denoted by the flat growth curve. De-protection of the tri-cyclic peptide polymer produces a positively charged polymer that exhibits an enhanced antimicrobial activity, inhibiting the growth of S. aureus at a concentration of 5 μg mL$^{-1}$.

Additionally, peptide nanopores can be functionalized with peptide sequences, or other antimicrobial agents, that promote recognition for bacterial cells and/or insertion into bacterial membranes to enhance the efficacy of the nanopores, or other therapeutic effects. The functionalization can occur via bonds that are robust (e.g., amide), susceptible to biodegradation (e.g., ester) for controlled-release, susceptible to degradation by external stimuli (e.g., photo-cleavable) for triggered-release, or a combination thereof.

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

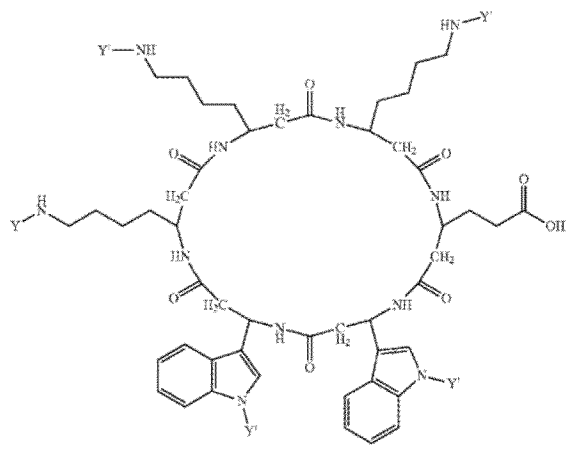

What is claimed is:

1. A cyclic peptide polymer having the structure:

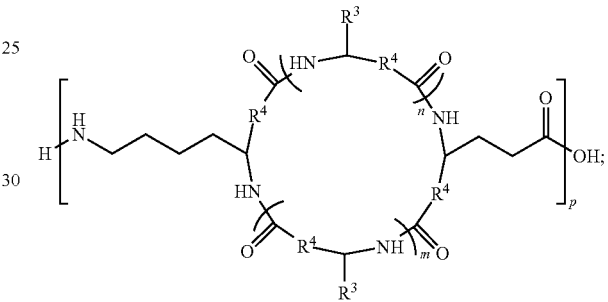

wherein each R$^3$ is an independently selected organic group;

wherein each R$^4$ is independently selected from covalent bond, methylene, ethylene, n-propylene, and n-butylene;

wherein m and n are nonnegative integers having a sum of at least 1; and wherein p is an integer greater than 1.

2. The cyclic peptide polymer of claim 1, wherein the cyclic peptide polymer has the structure:

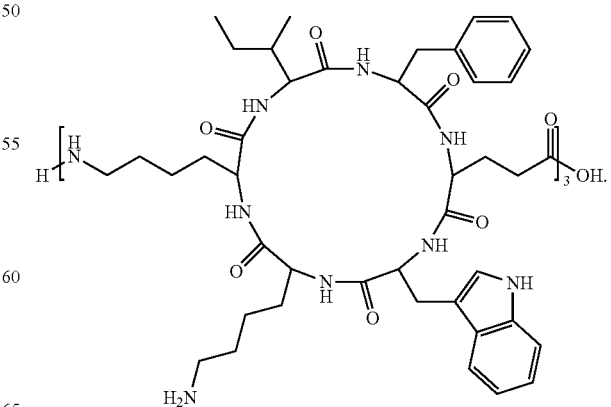

3. The cyclic peptide polymer of claim 1, wherein the cyclic peptide polymer has the structure:

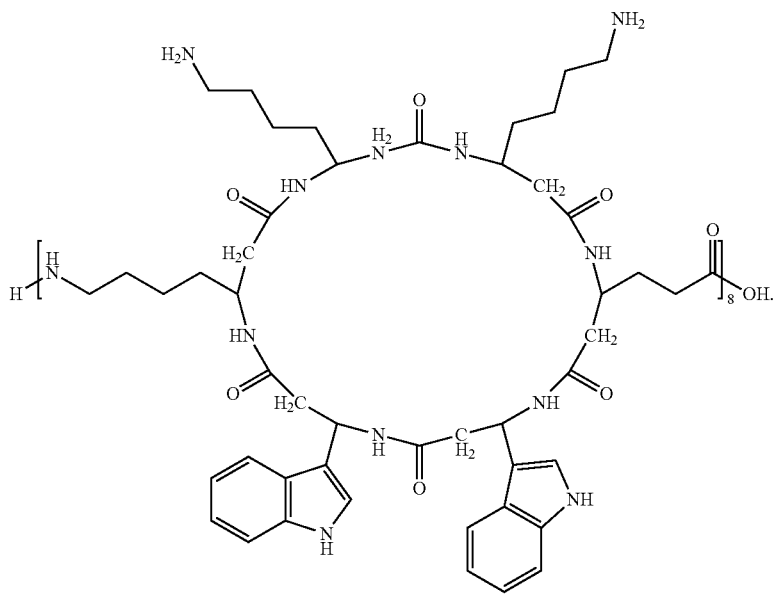

4. A cyclic peptide polymer having the structure:

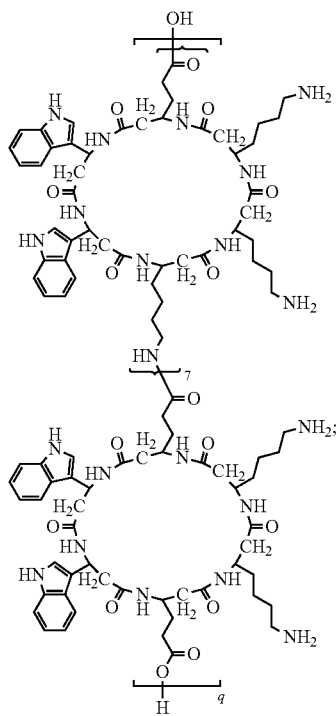

wherein q is a positive integer.

5. A method of making the cyclic peptide polymer of claim 1 comprising:
providing a first cyclic peptide monomer having the general structure:

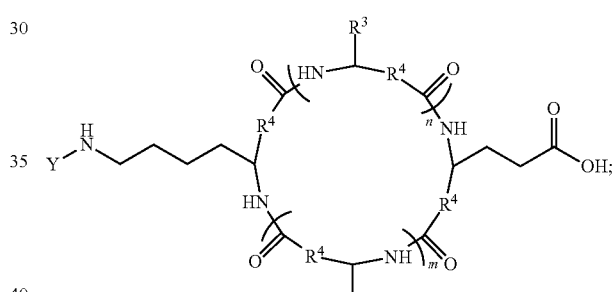

wherein Y is a protecting group;
covalently binding the —CO—OH group of the first cyclic peptide monomer to a solid support having a carboxylic acid-reactive group;
converting the —NH—Y group to —NH$_2$;
reacting the —NH$_2$ group with a —CO—OH group of an additional cyclic peptide monomer having the same general structure as the first cyclic peptide monomer;
wherein $R^3$, $R^4$, Y, m, and n of the additional cyclic peptide monomer may be the same or different from those of the first cyclic peptide monomer;
optionally repeating the converting and reacting steps with further additional cyclic peptide monomers; and
cleaving the cyclic peptide polymer from the solid support.

6. The method of claim 5, wherein the solid support comprises a 2-chlorotrityl chloride resin.

7. The method of claim 5, further comprising;
removing any protecting groups from the cyclic peptide polymer.

8. The method of claim 5, further comprising;
polymerizing the cyclic peptide polymer by reacting the —CO—OH group with the —NH$_2$ group.

9. The method of claim 5;
wherein the first cyclic peptide monomer has the structure:

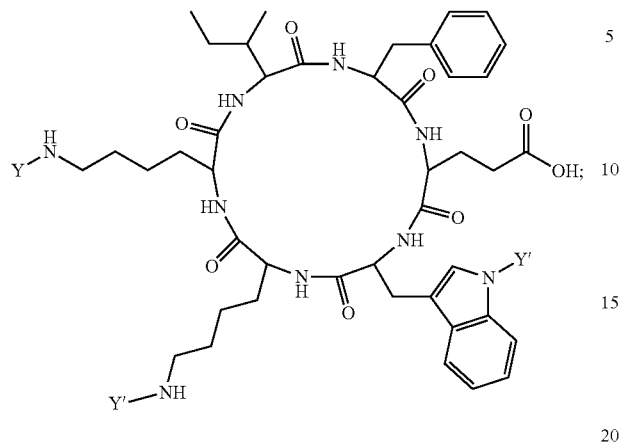
wherein each Y' is independently selected from H and a protecting group; and
wherein the cyclic peptide polymer consists of three repeat units of the first cyclic peptide monomer.
10. The method of claim 5;
wherein the first cyclic peptide monomer has the structure:
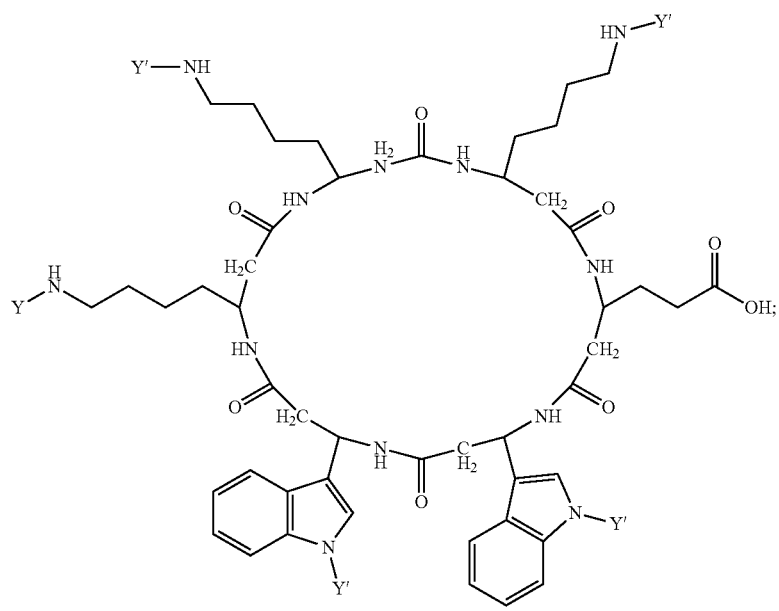

wherein each Y' is independently selected from H and a protecting group; and wherein the cyclic peptide polymer consists of eight repeat units of the first cyclic peptide monomer.

11. A method of making the cyclic peptide polymer of claim 4 comprising: providing a first cyclic peptide monomer having the structure:

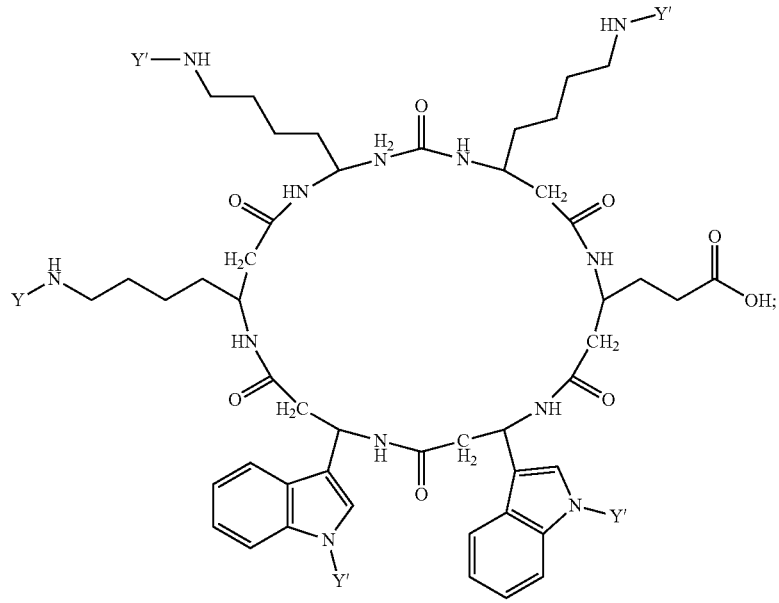

covalently binding the —CO—OH group of the first cyclic peptide monomer to a solid support having a carboxylic acid-reactive group;

converting the -NH-Y group to —NH2;

reacting the -NH2 group with a —CO—OH group of another first cyclic peptide monomer;

repeating the converting and reacting steps with further first cyclic peptide monomers;

converting the -NH-Y group to —NH2;

reacting the -NH2 group with a —CO—OH group of an additional cyclic peptide monomer having the structure:

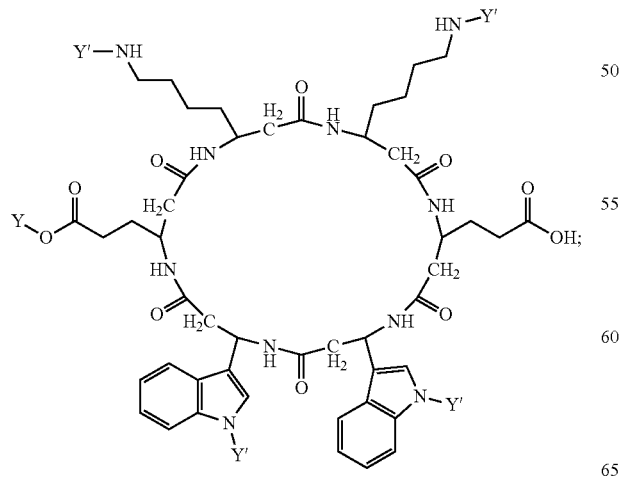

wherein each Y is a protecting group; and wherein each Y' is independently selected from H and a protecting group; converting each Y' to H; and cleaving the cyclic peptide polymer from the solid support;

wherein the cyclic peptide polymer consists of seven repeat units of the first cyclic peptide monomer and one repeat unit of the additional cyclic peptide monomer.

12. A cyclic peptide having the structure:

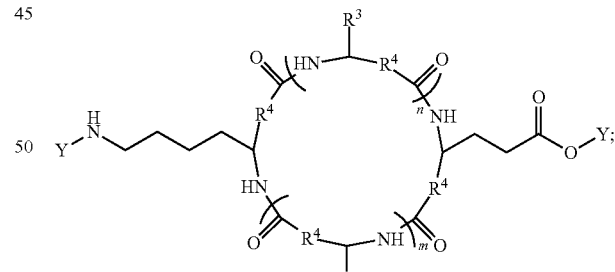

wherein each $R^3$ is an independently selected organic group;

wherein each $R^4$ is independently selected from covalent bond, methylene, ethylene, n-propylene, and n-butylene;

wherein m and n are nonnegative integers having a sum of at least 2; and wherein each Y is independently selected from H and a protecting group.

13. The cyclic peptide of claim 12, wherein the cyclic peptide has the structure:
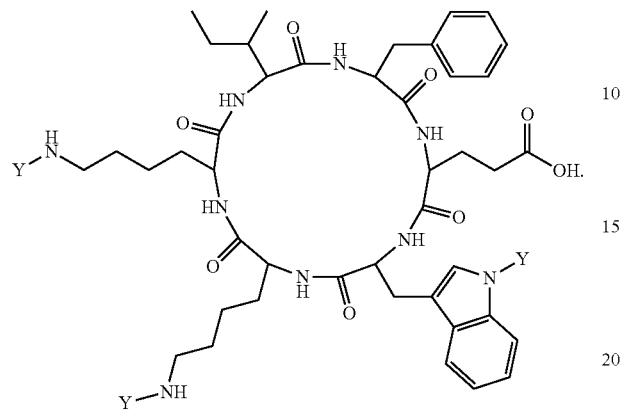
14. The cyclic peptide of claim 12, wherein the cyclic peptide has the structure:
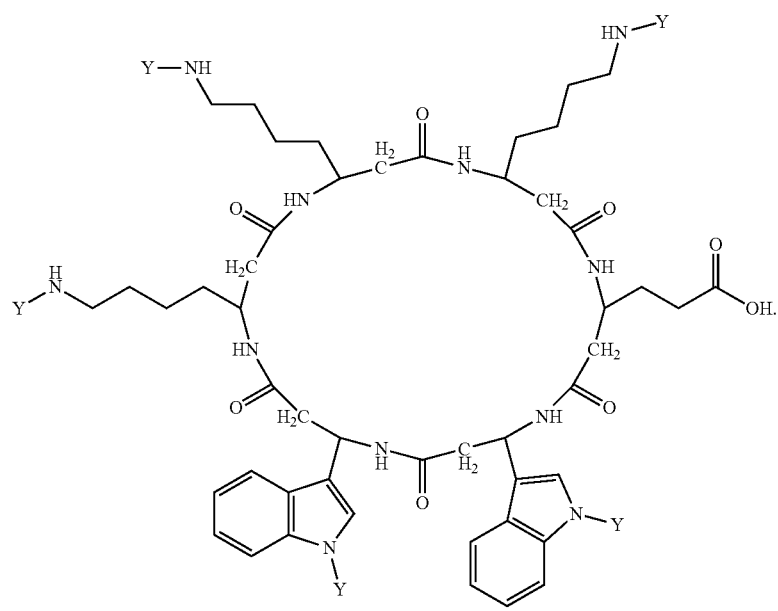

15. A cyclic peptide having the structure:
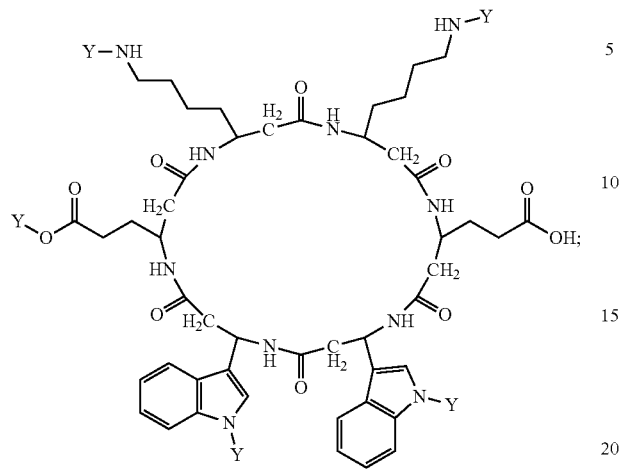
wherein each Y is independently selected from H and a protecting group.
16. A method of polymerizing the cyclic peptide of claim 12; wherein each Y is H.
* * * * *

UNITED STATES PATENT AND TRADEMARK OFFICE
CERTIFICATE OF CORRECTION

PATENT NO. : 11,447,524 B2  
APPLICATION NO. : 16/952876  
DATED : September 20, 2022  
INVENTOR(S) : Kenan P. Fears and Manoj K. Kolel-Veetil Page 1 of 3

It is certified that error appears in the above-identified patent and that said Letters Patent is hereby corrected as shown below:

In the Claims

In Claim 3, Column 11, Line 3:

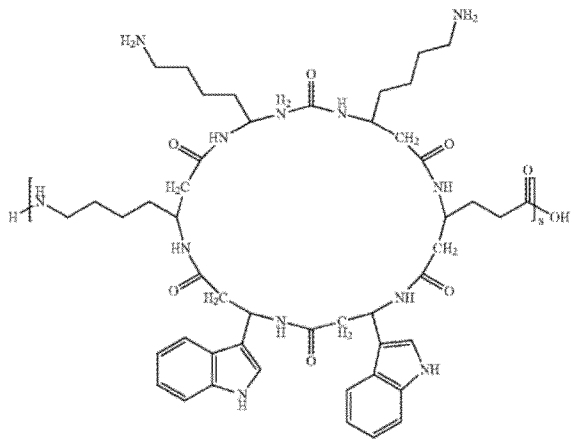

Should be:

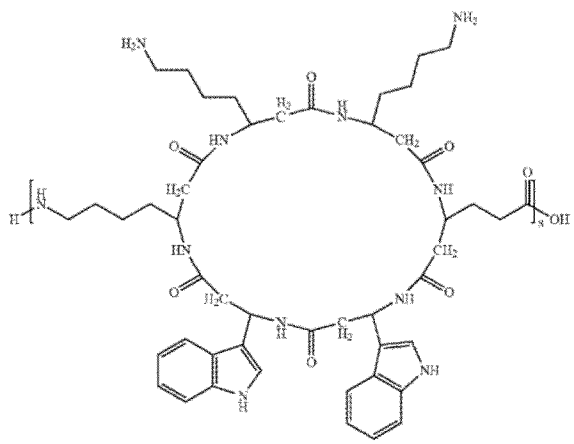

Signed and Sealed this  
Eighteenth Day of October, 2022

Katherine Kelly Vidal  
*Director of the United States Patent and Trademark Office*

In Claim 10, Column 13, Line 25:
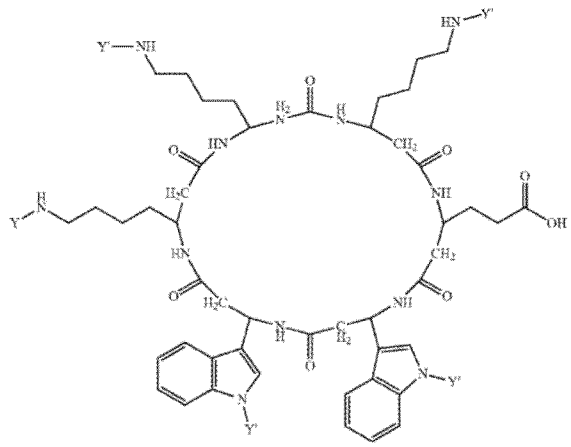
Should be:
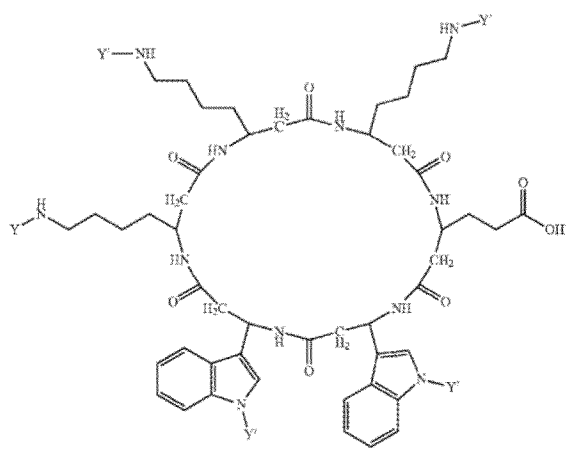
In Claim 11, Column 15, Line 8:
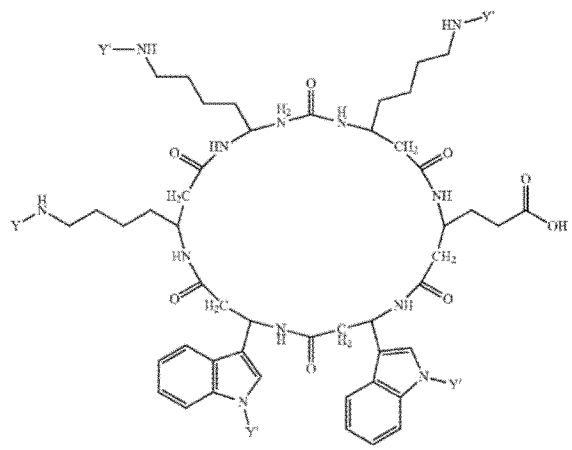

CERTIFICATE OF CORRECTION (continued)
U.S. Pat. No. 11,447,524 B2

Should be: